(12) United States Patent
Michelotti (10) Patent No.: US 10,494,765 B2
(45) Date of Patent: Dec. 3, 2019

(54) MONITORING SYSTEM FOR MONITORING THE CONDITIONS OF A BAND CIRCULATING IN A PAPER MAKING MACHINE AND PAPER MAKING MACHINE COMPRISING SAID SYSTEM

(71) Applicant: S.A. GIUSEPPE CRISTINI S.p.A., Milan (IT)

(72) Inventor: Matteo Michelotti, Pescia (IT)

(73) Assignee: S.A. GIUSEPPE CRISTINI S.P.A., Milan (IT)

( * ) Notice: Subject to any disclaimer, the term of this patent is extended or adjusted under 35 U.S.C. 154(b) by 296 days.

(21) Appl. No.: 15/325,780

(22) PCT Filed: Jul. 14, 2015

(86) PCT No.: PCT/IB2015/055324
§ 371 (c)(1),
(2) Date: Jan. 12, 2017

(87) PCT Pub. No.: WO2016/009354
PCT Pub. Date: Jan. 21, 2016

(65) Prior Publication Data
US 2017/0152631 A1    Jun. 1, 2017

(30) Foreign Application Priority Data
Jul. 14, 2014    (IT) .............................. MI14A001277

(51) Int. Cl.
*D21F 1/32*    (2006.01)
*D21G 9/00*    (2006.01)
*G01N 22/04*    (2006.01)
*G01N 33/34*    (2006.01)

(52) U.S. Cl.
CPC ........... *D21G 9/0036* (2013.01); *D21F 1/325* (2013.01); *G01N 22/04* (2013.01); *G01N 33/346* (2013.01)

(58) Field of Classification Search
CPC ................................................................
D21F 1/30; D21F 1/32; D21F 1/1325;
D21G 9/00; D21G 9/0009; D21G 9/0036;
D21G 9/0045; G01N 22/04; G01N 21/86;
G01N 2021/8663; G01N 21/89; G01N 33/346
USPC ................ 162/198, 252, 263, 199, 272, 274
See application file for complete search history.

(56) References Cited

U.S. PATENT DOCUMENTS

| | | | |
|---|---|---|---|
| 3,854,889 A | 12/1974 | Lemelson | |
| 3,972,624 A | 8/1976 | Klein et al. | |
| 5,070,556 A | 12/1991 | Gloger | |
| 7,678,233 B2 * | 3/2010 | Beselt | D21G 9/0027 162/198 |

(Continued)

FOREIGN PATENT DOCUMENTS

| | | |
|---|---|---|
| EP | 1 275 772 | 1/2003 |
| EP | 1 342 839 | 9/2003 |

(Continued)

*Primary Examiner* — Eric Hug
(74) *Attorney, Agent, or Firm* — Leason Ellis LLP (57) ABSTRACT

A monitoring system for monitoring the conditions of a band circulating in a paper making machine is provided with: a detecting device configured to detect at least one parameter indicative of the conditions of the band; and with a moving assembly configured to move the detecting device along a direction transversal to the circulating direction of the band and comprising a cable moving device.

10 Claims, 6 Drawing Sheets

(56) References Cited

U.S. PATENT DOCUMENTS

2014/0345397 A1* 11/2014 Beselt .................. D21G 9/0009
73/866.5

FOREIGN PATENT DOCUMENTS

| WO | WO 2006/034267 | 3/2006 |
| WO | WO 2012/035521 | 3/2012 |

* cited by examiner

MONITORING SYSTEM FOR MONITORING THE CONDITIONS OF A BAND CIRCULATING IN A PAPER MAKING MACHINE AND PAPER MAKING MACHINE COMPRISING SAID SYSTEM

CROSS REFERENCE TO RELATED APPLICATIONS

The present application is a U.S. National Phase of International Patent Application PCT/IB2015/055324, filed on Jul. 14, 2015, which claims priority to Italian Application No. MI2014A001277, filed on Jul. 14, 2014, each of which is incorporated by reference as if expressly set forth in their respective entireties herein.

TECHNICAL FIELD

The present invention relates to a monitoring system for monitoring the conditions of a band circulating in a paper making machine and to a paper making machine comprising said system.

BACKGROUND ART

As is known, conventional paper making machines use belts (commonly called bands) circulating along closed loop paths and by means of which the paper material being formed is transported and processed.

Each section of the machine generally has a specific type of band.

To obtain high quality paper it is important to evaluate the conditions of the band in each section, as well as to monitor the conditions of the material transported thereon. The conditions of the band, in terms of water absorption, water transport and water permeability influence the quality of the sheet of paper during the pressing step. Therefore, it is important to monitor the conditions of the band for manufacturing the paper.

Normally, the conditions of bands circulating in paper making machines are monitored by means of detecting devices, configured to detect parameters indicating the conditions of the band, such as humidity, permeability, presence of contaminants, etc.

The detecting devices are usually fixed or are moved manually by an operator, who, if necessary, places them in proximity of the band, or directly in contact with the band, to carry out the necessary measurements.

It is often necessary to perform scans along directions transversal to the circulating direction of the band to detect the operating conditions of the band along the whole of its width. However, manual movement of the detecting device does not allow these measurements to be carried out in a manner that is repeatable and, above all, guaranteeing the safety of operators.

DISCLOSURE OF INVENTION

Therefore, an object of the present invention is to produce a monitoring system to monitor the conditions of a band circulating in a paper making machine without the aforesaid problems of the prior art; in particular, it is an object of the invention to produce a monitoring system for monitoring the conditions of a band circulating in a paper making machine that enables the aforesaid problems to be overcome in a simple and inexpensive manner, both from a functional point of view and in terms of construction.

In accordance with these objects, the present invention relates to a monitoring system for monitoring the conditions of a band circulating in a paper making machine as claimed in claim 1.

A further object of the invention is to provide a paper making machine in which monitoring of the conditions of the band can be performed in a simple manner and, at the same time, guaranteeing the safety of the operators involved.

In accordance with these objects, the present invention relates to a paper making machine in accordance with claim 12.

BRIEF DESCRIPTION OF THE DRAWINGS

Further features and advantages of the present invention will be apparent from the description below of a non-limiting example of embodiment thereof, with reference to the figures of the accompanying drawings, wherein.

BEST MODE FOR CARRYING OUT THE INVENTION

Figure 1:
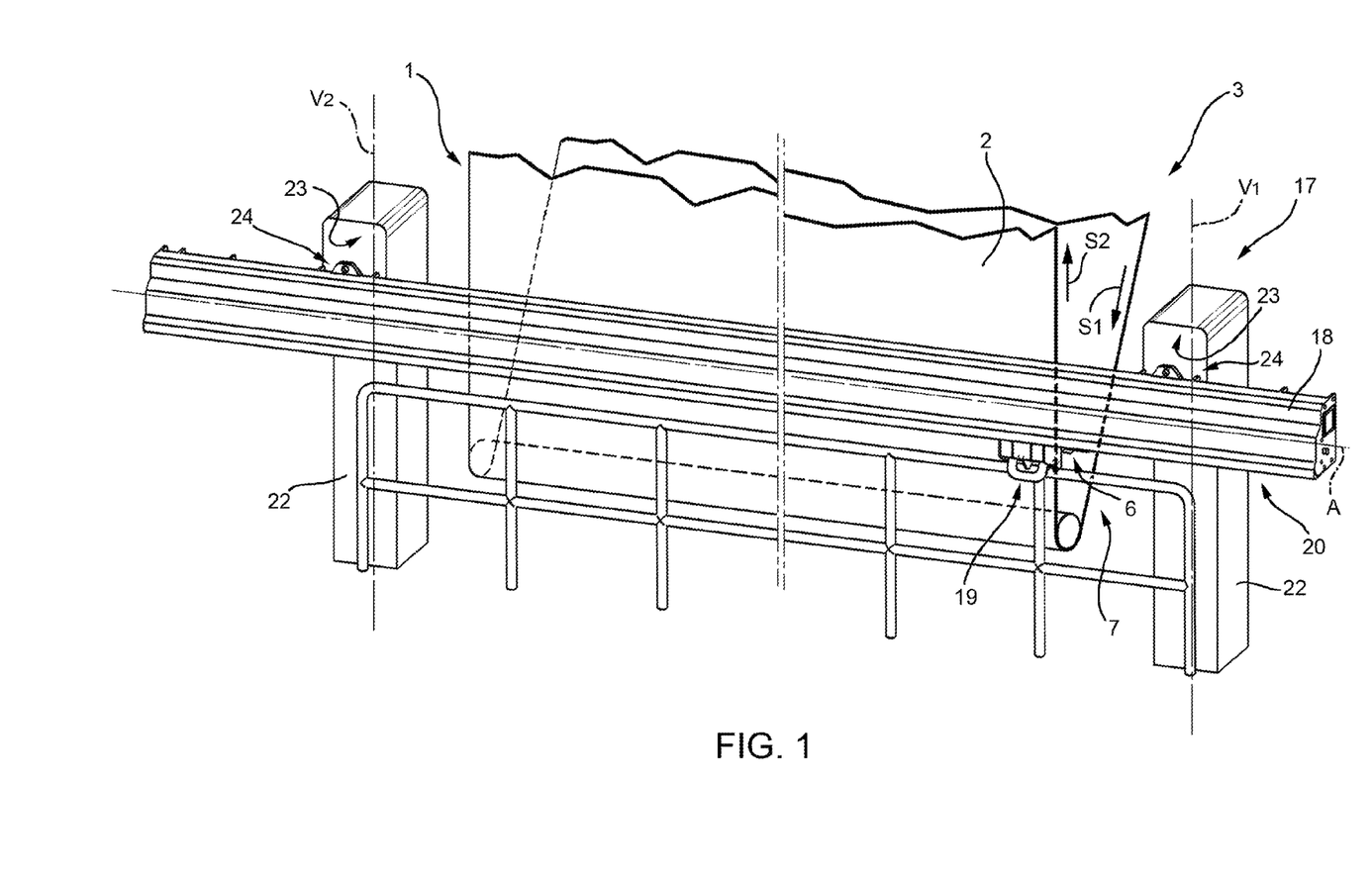
FIG. 1 is a perspective view with parts removed for clarity of the monitoring system for monitoring the conditions of a band according to the present invention.

FIG. 1 indicates with the reference numeral 1 a monitoring system for monitoring the conditions of a band 2 circulating in a paper making machine 3 according to the present invention.

FIG. 1 illustrates only a portion of the paper making machine 3 comprising a band 2 and a return roller 4 around which the band 2 circulates. The band 2 is circulated along a first circulating direction S1 upstream of the return roller 4 and along a second circulating direction S2 downstream of the return roller 4.

In the non-limiting example described and illustrated here, the portion of the paper making machine 3 illustrated in FIG. 1 belongs to a press section and the portion of the machine illustrated in FIG. 1 is located in a position upstream of one of the presses of the pressing station. It is understood that the system 1 according to the present invention can also be installed in the drying sections and/or in the forming sections of the paper making machine 3.

The system 1 comprises a detecting device 6 configured to detect at least one parameter indicative of the conditions of the band 2 and a moving assembly 7 configured to move the detecting device 6 with respect to the band 2.

In the non-limiting example described and illustrated here, the detecting device 6 is provided with a first detector (not illustrated) configured to detect the humidity of the band 2, with a second detector (not illustrated) configured to detect the permeability of the band 2 and with a third detector configured to measure the temperature of the band 2. In particular, the first detector comprises at least one microwave sensor while the second detector comprises at least one water dispensing nozzle and one flow measuring device associated with the nozzle. The detecting device 6 also comprises a control unit (not illustrated), connected to the detectors to process signals coming from them.

Preferably, the detecting device 6 is fed with water by means of a water supply line 5 (visible in FIGS. 5 and 6) and is provided with a battery power supply. In a variant it is connected to the electricity supply network by means of a cable.

In a further variant, not illustrated, the control unit is arranged in a remote seat and communication between the control unit and the detectors of the detecting device 6 takes place via cable or via wireless communication systems.

It is understood that the detecting device 6 can detect other parameters indicative of the conditions of the band 2.

Figures 4, 10:
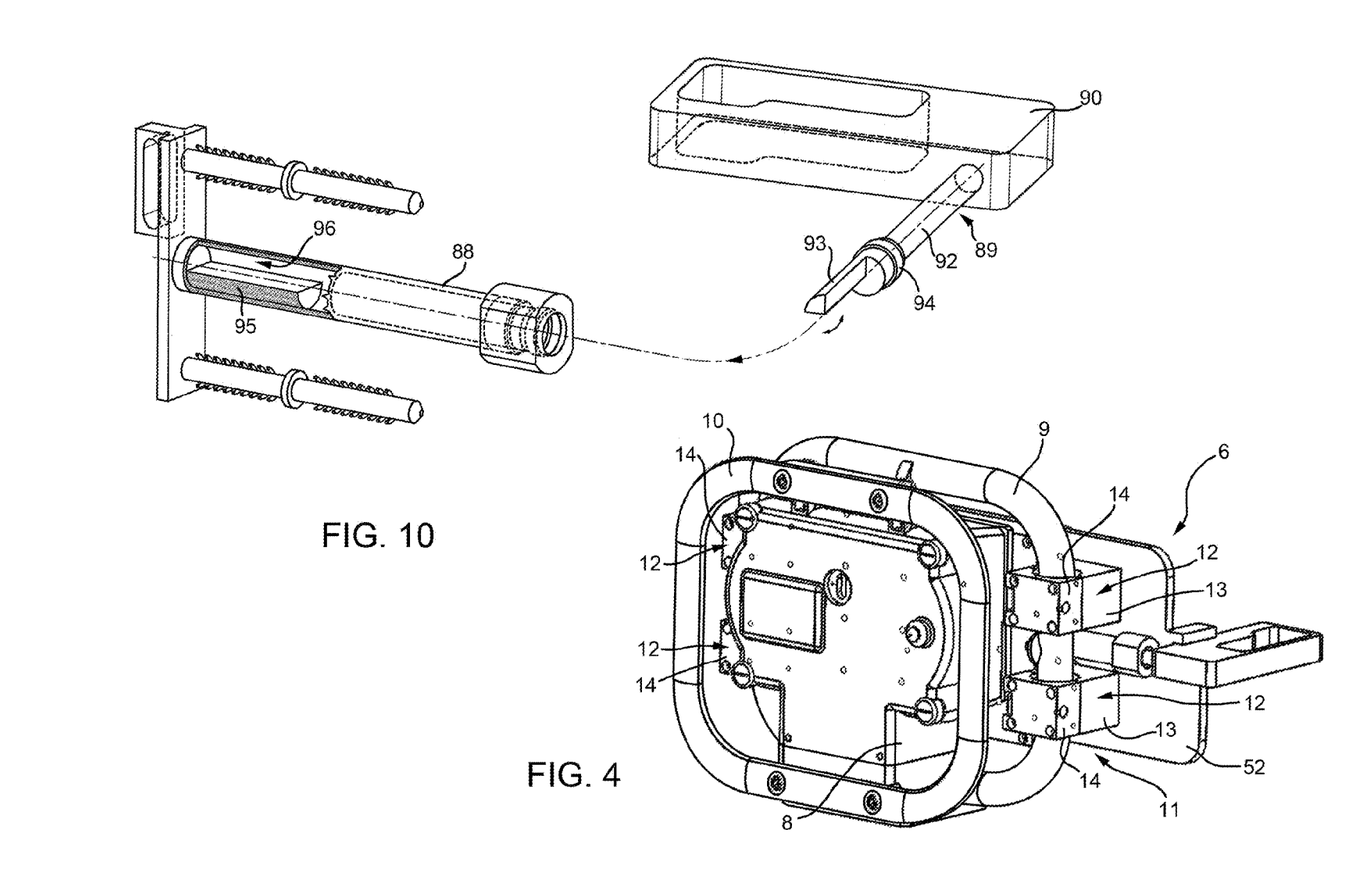
FIG. 4 is a perspective view, with parts in cross section and parts removed for clarity, of a third detail of the system of FIG. 1.
FIG. 10 is an exploded perspective view, with parts in cross section and parts removed for clarity, of a sixth detail of the system of FIG. 1.

With reference to FIG. 4, the detecting device 6 comprises a case 8, inside which the first, the second and the third detector and the control unit are housed, a handle 9 that can be gripped by an operator to manually manoeuvre the detecting device 6, a perimeter frame 10 arranged around the case 8 and a binding element 11.

In the non-limiting example described and illustrated here, the binding element 11 is defined by four binding element blocks 12 fixed to the handle 9.

In particular, the binding element blocks 12 are defined by a first jaw 13 and by a second jaw 14 clamped around the handle 9. As will be seen in detail below, the first jaw 13 of each binding element block 12 is provided with a recess 15 (visible in FIGS. 8 and 9).

With reference to FIG. 1, the moving assembly 7 comprises a supporting frame 17, a guide 18 supported by the supporting frame 17, a carriage 19 movable along the guide 18, and a moving device 20 configured to move the carriage 19 along the guide 18.

The supporting frame 17 comprises two substantially identical uprights 22, which are preferably arranged parallel resting on the floor or on a suitable support base at the sides of the band 2. Preferably the uprights 22 extend along two respective vertical axes $V_1$ and $V_2$.

The uprights 22 are preferably in the shape of a parallelepiped and are respectively provided with a coupling face 23 able to be coupled to the guide 18 by means of respective coupling means 24.

Preferably the coupling means 24 comprise screw coupling systems, not visible in the accompanying figures.

In a variant not illustrated, the uprights are shaped, for example, so as to define a housing seat able to house and to support the guide 18.

The uprights 22 are preferably hollow to allow parts of the system 1 to be housed therein, if necessary.

In a variant not illustrated, the supporting frame 17 is a portion of the main frame normally used also to support other elements of the paper making machine 3.

The guide 18 extends along an axis A, orthogonal to the axes $V_1$ $V_2$ of the uprights 22 and, therefore, extends horizontally.

In other words, the guide 18 and the uprights 22 define a bridge structure.

In the non-limited example described and illustrated here, the guide 18 is arranged in front of the band 2, which substantially slides along an almost vertical direction S2.

It is understood that the structure defined by the uprights 22 and by the guide 18 can be shaped and arranged so that the band 2 is located below the guide 18, or even above the guide 18.

Figure 5:
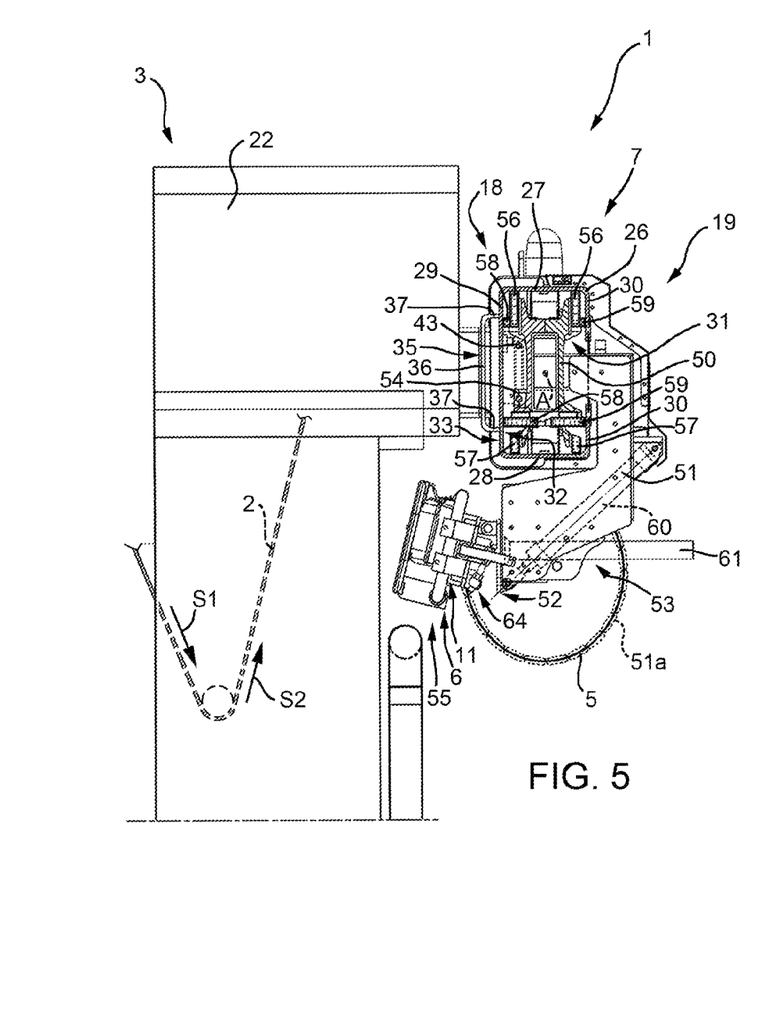
FIG. 5 is a side view, with parts in cross section and parts removed for clarity, of the system of FIG. 1 in a first operating position.

With reference to FIG. 5, the guide 18 comprises a guide element 26, which extends along the axis A and has a substantially C-shaped cross section, along a plane orthogonal to the axis A.

In particular, the guide element 26 comprises an upper wall 27, a lower wall 28 parallel to the upper wall 27, a lateral wall 29, coupled to the upper wall 27 and to the lower wall 28 and orthogonal to both, and two lateral appendices 30, which project orthogonally respectively from the upper wall 27 and from the lower wall 28.

Preferably, the guide element 26 is produced in one piece.

The guide element 26 thus shaped defines a longitudinal seat 31 delimited by the upper wall 27, by the lower wall 28, by the lateral wall 29 and by the two lateral appendices 30.

The lateral wall 29 has an inner face 32, which faces the seat 31 and an outer face 33, which is coupled to the coupling faces 23 of the uprights 22. In particular, the stretch of the outer face 33 comprised between the uprights 22 is coupled to a stiffening element 35, which is configured to increase the rigidity of the guide element 26.

In particular, the stiffening element 35 extends parallel to the longitudinal axis A and has a substantially U-shaped cross section, along a plane orthogonal to the axis A.

The stiffening element 35 thus comprises a longitudinal wall 36 and a plurality of longitudinal appendices 37 that project from the longitudinal wall 36 and are coupled to the outer face 33 of the lateral wall 29. The coupling between the longitudinal appendices 37 and the lateral wall 29 is preferably obtained by welding.

Figure 2:
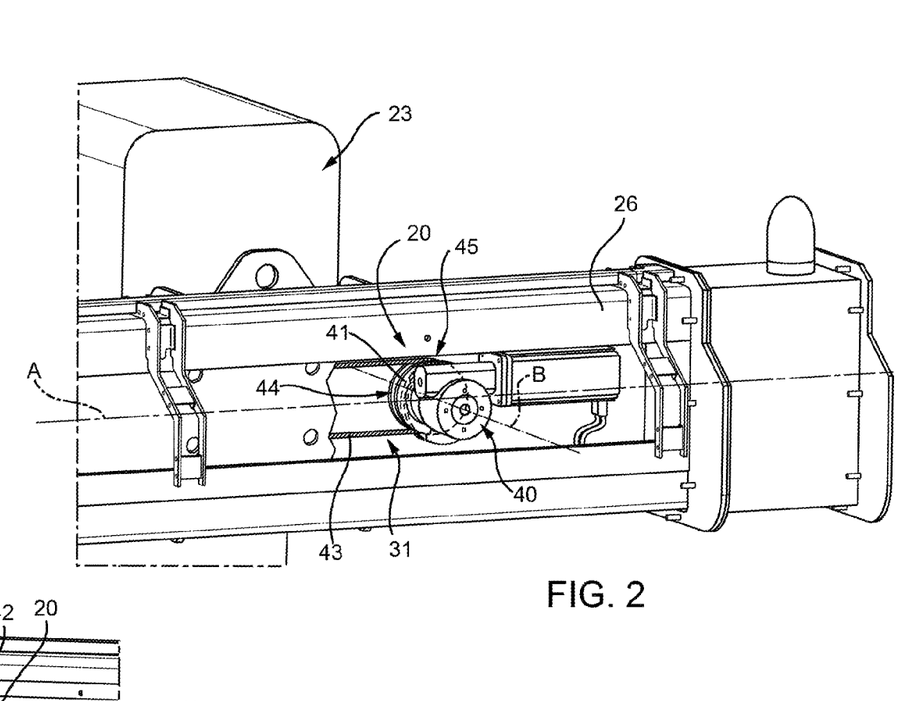
FIG. 2 is a perspective view, with parts in cross section and parts removed for clarity, of a first detail of the system of FIG. 1.
Figure 3:
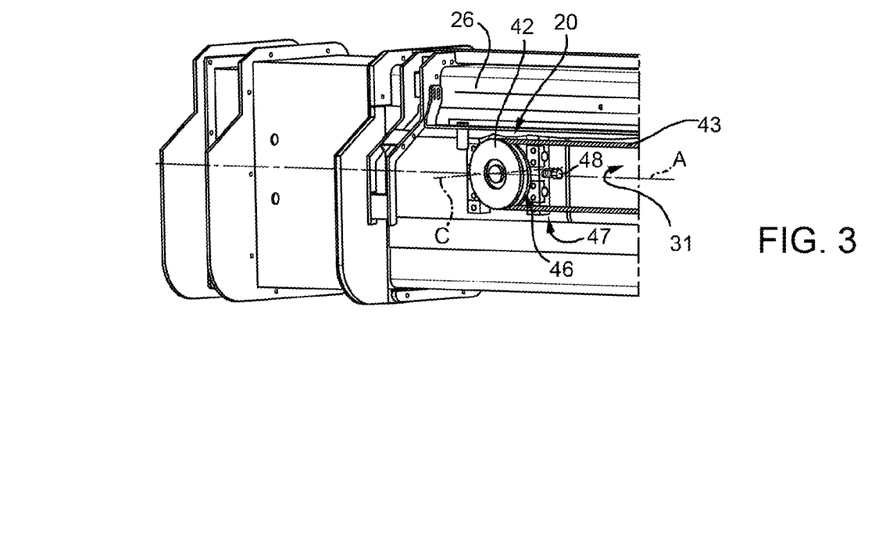
FIG. 3 is a perspective view, with parts in cross section and parts removed for clarity, of a second detail of the system of FIG. 1.

With reference to FIGS. 2 and 3, the moving device 20 is a cable moving device comprising a moving member 40 arranged in the seat 31 in proximity of an upright 22, a moving pulley 41, a return pulley 42 arranged in the seat 31 in proximity of the other upright 22 and a hauling cable 43.

The moving pulley 41 is rotatable about a rotation axis B orthogonal to the axis A and is moved by the moving member 40 connected to the moving pulley 41 via transmission means (not illustrated). The moving pulley 41 comprises a substantially circular outer edge 45, which is provided with a housing seat 44 configured to house the hauling cable 43.

The moving member 40 is preferably a stepper motor and is associated with a system for detecting the position of the carriage 19 along the guide 18.

The return pulley 42 is rotatable about an axis C, has a housing seat 46 configured to house the hauling cable 43 and rotates idle drawn by the hauling cable 43.

The return pulley 42 is preferably coupled to a tensioner 47, configured so as to adjust the position of the return pulley 42 along the axis A. In particular, axial adjustment takes place through screwing of the threaded pin 48.

The hauling cable 43 is preferably a steel cable. The moving pulley 41 and the return pulley 42 are preferably rubber coated.

Figure 6:
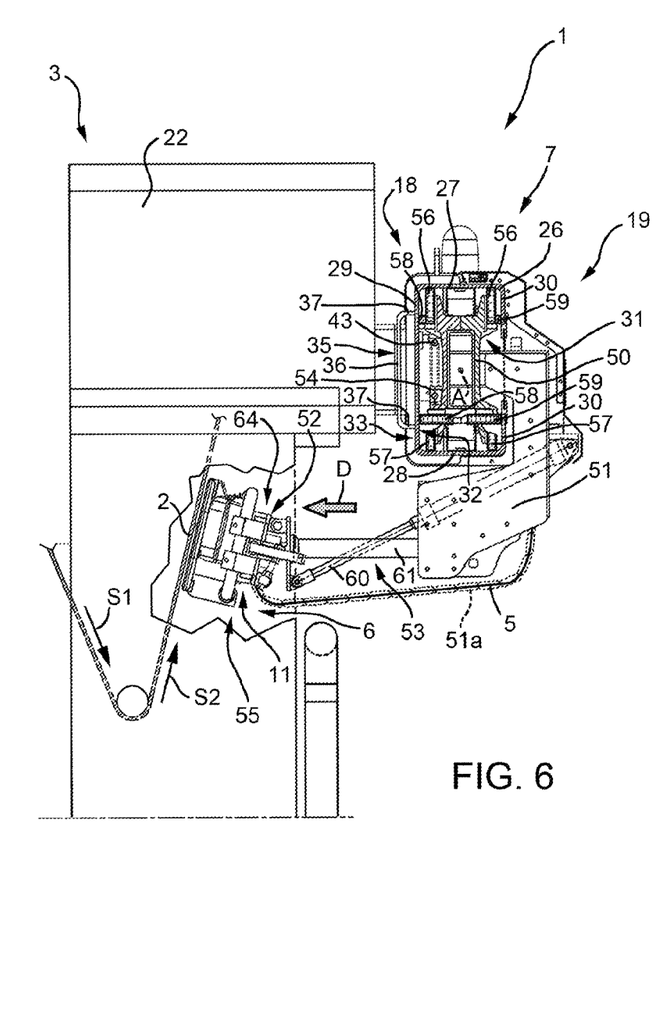
FIG. 6 is a side view, with parts in cross section and parts removed for clarity, of the system of FIG. 1 in a second operating position.

With reference to FIG. 5 and FIG. 6, the carriage 19 comprises a main body 50, a supporting arm 51, a binding element 52 able to be coupled to the binding element 11 of the detecting device 6, shifting means 53 configured to shift the binding element 52, and a grip member 54 configured to hook the carriage 19 to the hauling cable 43.

The carriage 19 also comprises a blocking device 55, configured to selectively fix the binding element 11 to the binding element 52.

In a variant not illustrated, the blocking device is comprised in the detecting device and not in the carriage.

In the non-limiting example described and illustrated here, the carriage 19 is also provided with an articulated cable grommet 51a, coupled to one side of the supporting arm 51 and configured to house the water supply line 5 of the detecting device 6 and any other service cables.

The main body 50 is housed in the seat 31 and slides inside the seat 31 along the axis A due to the presence of a plurality of first wheels 56 arranged preferably vertical and rotatable resting on the upper wall 27 of the guide element 26, a plurality of second wheels 57 arranged preferably vertical and rotatable resting on the lower wall 28 of the guide element 26, a plurality of third wheels 58 arranged preferably horizontal and rotatable resting on the lateral wall 29 of the guide element 26 and a plurality of fourth wheels 59 arranged preferably horizontal and rotatable resting on the appendices 30 of the guide element 26.

In the non-limiting example described and illustrated here the main body 50 is provided with four first wheels 56, with four second wheels 57, with four third wheels 58 and with four fourth wheels 59. The presence of the wheels 56, 57, 58 and 59 stabilizes sliding of the carriage 19 along the guide 18.

The grip member 54 is preferably coupled to the face of the main body 50 arranged in front of the inner face 32 of the lateral wall 29 of the guide element 26. Preferably, the grip member 54 is associated with a tightening element (not visible in the accompanying figures) configured to tighten the hauling cable 43 if required.

Preferably, the main body is coupled to two protective covers (not visible in the accompanying figures) configured to protect the seat 31 from processing residues, contaminants, dust, etc. In this way, the area in which the hauling cable 43 circulates is kept clean. Moreover, the protective covers substantially close the seat 31, allowing controlled pressurisation of the seat 31 in the case in which this is considered necessary.

In detail, the protective covers are defined by thin metal sheets having one end coupled to a rotating shaft arranged at the ends of the guide 18 and one end coupled to the carriage. The movement of the carriage causes unwinding of one cover and winding of the other cover guaranteeing protection of the seat 31 for the whole of its length.

The supporting arm 51 is coupled to the main body 50 and is shaped so as to define a central seat and two lateral seats (not clearly visible in the accompanying figures) able to house the shifting means 53 of the binding element 52.

In particular, the shifting means 53 comprise an actuator 60, preferably pneumatic, coupled to the binding element 52 and housed inside the central seat of the supporting arm, and two supporting pins 61 (only one of which is visible in the accompanying figures), coupled to the binding element 52, housed in the lateral seats of the supporting arm 51 and guided slidingly by rollers of the supporting arm (not illustrated in the accompanying figures).

In use, operation of the actuator 60 causes shifting of the binding element 52 along the sliding direction D of the supporting pins 61 (FIG. 6).

In the non-limiting example described and illustrated here, the sliding direction D of the supporting pins 61 is substantially orthogonal to the axis A.

In other words, operation of the actuator 60 causes shifting of the binding element 52, and consequently of the detecting device 6 coupled thereto, along a direction D orthogonal to the axis A.

Shifting of binding element 52 causes, in use, shifting of the detecting device 6 and is adjusted so that the detecting device 6 is arranged at a distance from the band 2 necessary to perform the detection operations. In the non-limiting example described and illustrated here, the detecting device 6 is arranged, in use, substantially in contact with the band 2 as illustrated in FIG. 6.

Figure 7:
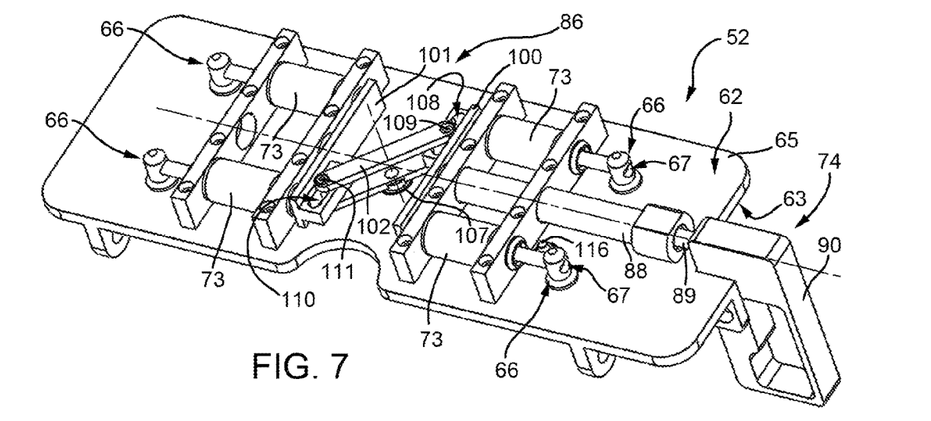
FIG. 7 is a perspective view, with parts removed for clarity, of a fourth detail of the system of FIG. 1.
Figure 8:
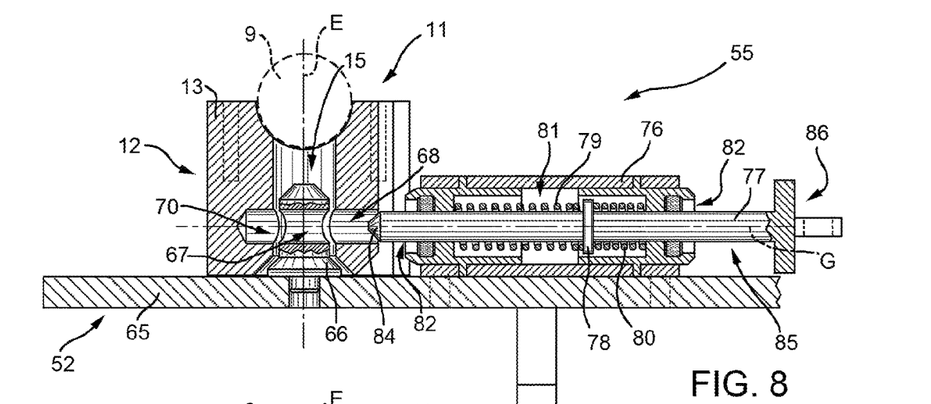
FIG. 8 is a cross sectional view, with parts removed for clarity, of a fifth detail of the system of FIG. 1 in a first operating position.
Figure 9:
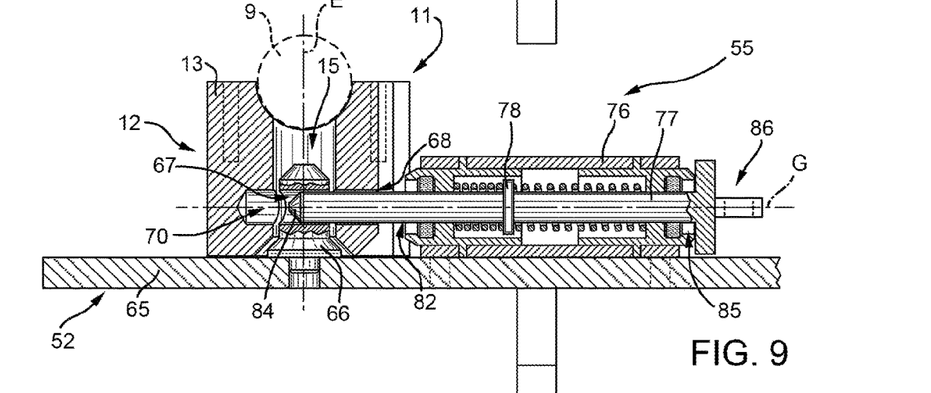
FIG. 9 is a cross sectional view, with parts removed for clarity, of the fifth detail of FIG. 8 in a second operating position.

With reference to FIG. 7, the binding element 52 comprises a plate 65, which is provided with a coupling face 62 and with a supporting face 63 coupled, via connecting means 64 (FIGS. 5-6), to the actuator 60 and to the supporting pins 61, and a plurality of protrusions 66, which project from the coupling face 63 and are shaped so as to define a geometric coupling with the recesses 15 of the binding element 11 of the detecting device 6 as also illustrated in FIGS. 8 and 9.

The connecting means 64 preferably comprise an angular adjustment device (not clearly visible in the accompanying figures), configured to adjust the angular position of the plate 65 with respect to the sliding direction D of the supporting pins 61.

The protrusions 66 are arranged on the coupling face 63 substantially at the vertices of a quadrilateral.

In a variant not illustrated, the binding element 52 is provided with recesses and the binding element 11 is provided with protrusions configured so as to define a geometric coupling with the recesses of the binding element 52.

With reference to FIGS. 8 and 9, the binding element 11 and the binding element 52 are configured so as to define a geometric coupling between each other. The geometric coupling speeds up the operations of positioning of the detecting device 6 on the carriage 19.

In the non-limiting example described and illustrated here, the protrusions 66 are definite substantially by cylindrical pins and the recesses 15 are defined by holes with a substantially cylindrical cross section extending along an axis E.

The protrusions 66 are provided with a through hole 67. The recesses 15 are provided with a lateral opening 68, preferably having a cylindrical cross section and extending along a direction orthogonal to the axis E.

When geometrically coupled, the recesses 15 and the protrusions 66 give rise to a blocking hole 70, defined by alignment of the lateral opening 68 and of the through hole 67, able to cooperate with the blocking device 55.

With reference to FIG. 7, the blocking device 55 comprises a plurality of blocking elements 73 and an actuator 74, configured to shift simultaneously the blocking elements 73 between a unblocking position, wherein the binding element 11 is not fixed to the binding element 52 and a blocking position wherein the binding element 11 is fixed to the binding element 52.

The blocking elements 73 are preferably four and are configured to cooperate, in use, with a respective blocking hole 70 defined by alignment of the lateral opening 68 and of the through hole 67.

With reference to FIGS. 8 and 9, each blocking element 73 comprises a cylinder 76, a piston 77 housed partially in the cylinder 76 and moving in the cylinder 76, a stop ring 78 coupled to the piston 77, a first spring 79 and a second spring 80.

The cylinder 76 is defined by a hollow main body extending along a longitudinal axis G, which defines a seat 81 inside which the piston 77 is partially housed. The cylinder 76 is provided with two openings 82 produced on the opposite base walls and substantially aligned along the axis G and engaged, in use, by the piston 77.

Each cylinder 76 is supported by the plate 65 and is arranged in proximity of a respective protrusion 66 substantially inside the quadrilateral defined by the protrusions 66.

The first spring 79 is arranged around the piston 77 inside the seat 81 between the stop ring 78 and the base wall of the cylinder 76 arranged in proximity of the respective protrusion 66, while the second spring 80 is arranged around the piston 77 inside the seat 81 between the stop ring 78 and the base wall of the cylinder 76 distal with respect to the respective protrusion 66.

The piston 77 is provided with a first substantially pointed end 84 and with a second end 85 coupled to the actuator 74 by means of a transmission system 86 that will be described in detail below.

In use, the cylinder 77 is operated by the actuator 74 to cooperate selectively with the respective blocking hole 70.

In particular, in the unblocking position illustrated in FIG. 8, the first end 84 partially engages the blocking hole 70; in particular the first end 84 partially engages only the lateral opening 68. In fact, in the unblocking position the piston 77 is moved slightly forward inside the blocking hole 70. This aspect does not prejudice the geometric coupling between the recesses 15 and the protrusions 66, as the end 84 produces a quick release blocking.

In fact, in use when the block 12 is moved towards the protrusion 66, the piston 77 is moved back by the block 12 due to the pointed shape of the first end 84. Instead, the spring 80 pushes the end 84 until the end is aligned with the blocking hole 80.

Similarly, detachment between the block 12 and the protrusion 66 is not obstructed by the presence of the first end 84 of the piston 77. In fact, during detachment, the piston 77 is moved back by the block 12 due to the combination of the pointed shape of the first end 84 and of the suitable shape of the block 12.

This quick release coupling facilitates positioning of the detecting device on the carriage 19 and ensures that the subsequent blocking operations take place correctly and without decelerations.

In the blocking position illustrated in FIG. 9, the piston 77 completely engages the blocking hole 70, and in particular engages both the lateral opening 68 and the through hole 67. In this way, detachment between the block 12 and the protrusion 66 is prevented.

Passage from the blocking position to the unblocking position is also facilitated by the presence of the spring 79, which pushes the piston 77 out of the blocking hole 70 as soon as the pushing action of the actuator 74 ceases.

As already mentioned, the actuator 74 is configured to operate simultaneously the pistons 77 of each blocking element 73 due to a transmission system 86.

With reference to FIG. 7, the actuator 74 comprises a cylinder 88 inside which there is housed a shaft 89 connected to a handle 90 and configured to rotate inside the cylinder 88 by a maximum angle of 90°. The cylinder 88 is fixed to the transmission system 86.

As will be described in detail below, a pulling action by an operator on the handle 90 causes operation of the transmission system 86 to shift the blocking elements 73 from the unblocking position to the blocking position; the consequent action of rotating the handle 90 instead causes blocking of the blocking elements 73 in the blocking position.

With reference to FIG. 10, the shaft 89 is provided with a first cylindrical portion 92 and with a second portion 93 having a quadrant cross section. A stop ring 94 is produced between the first cylindrical portion 92 and the second portion 93.

The cylinder 88 is hollow and is provided internally with a semi-cylindrical fixed insert 95 able to define a housing seat 96, also semi-cylindrical. In use, the shaft 89 is inserted inside the cylinder 88 so that the second portion 93 is housed in the semi-cylindrical housing seat 96. In this way, the shaft 89 can rotate through a maximum of 90°. Preferably, the shaft 89 can slide inside the cylinder 88. Sliding of the shaft 89 inside the cylinder 88 is limited by the presence of a spring (not illustrated) arranged around the first cylindrical portion 92 of the shaft inside the cylinder 89. Moreover, the spring facilitates the return movement of the shaft 88 inside the cylinder 89 after the pulling action on the handle 90 by the operator has been completed.

With reference to FIGS. 11-14, the transmission system 86 comprises a main plate 100, fixed to which are the cylinder 88 and the pistons 77 of two of the blocking elements 73, a secondary plate 101, fixed to which are the pistons 77 of the other two blocking elements 73, and a lever 102.

The lever 102 is provided with a first end 104 coupled to the main plate 100, with a second end 105 coupled to the secondary plate 101 and with a central pivot 106 coupled to a pin 107 that projects from the coupling face 62 of the plate 65.

The main plate 100 is provided with a slot 108 engaged by a first pin 109 that projects from the first end 104 of the lever 102 while the secondary plate 101 is provided with a slot 110 engaged by a second pin 111 that projects from the second end 105 of the lever 102.

Figure 11:
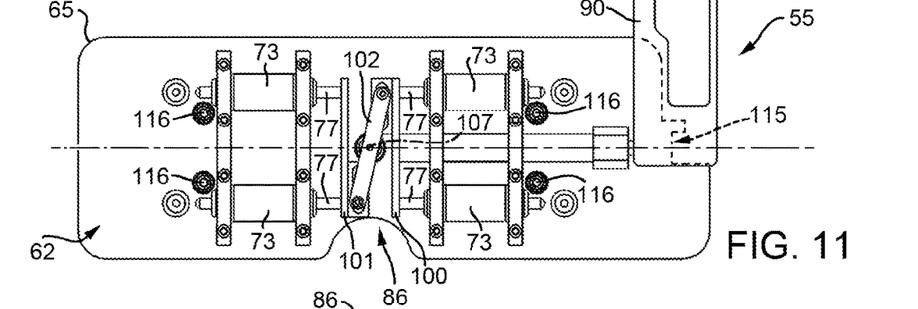
FIGS. 11-14 are top views of the fourth detail of FIG. 7 in four different operating positions.

FIG. 11 illustrates the unblocking position in which the handle 90 is free and is not subjected to pulling by the operator.

Figure 12:
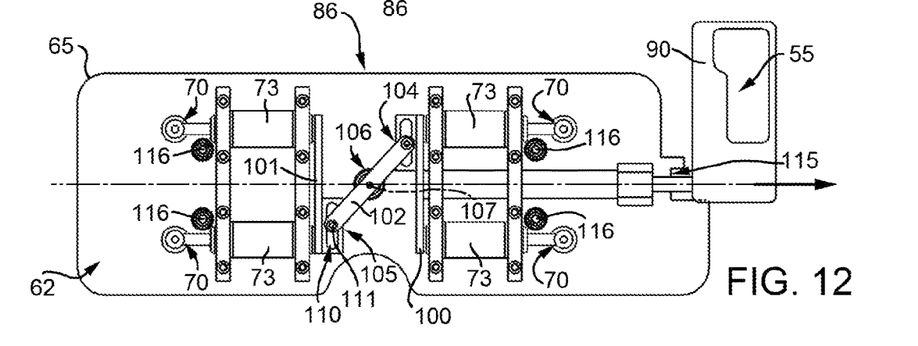

FIG. 12 illustrates the pulling movement on the handle 90 that causes shifting of the blocking elements 73 from the unblocking position to the blocking position in which the pistons 77 engage the blocking holes 70.

Figure 13:
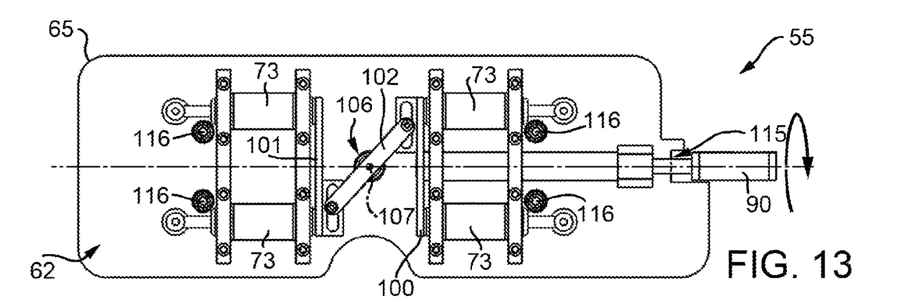

The simultaneous rotation of the handle through 90° allows the handle to be housed inside a groove 115 suitably produced in the plate 65 (FIG. 13).

Figure 14:
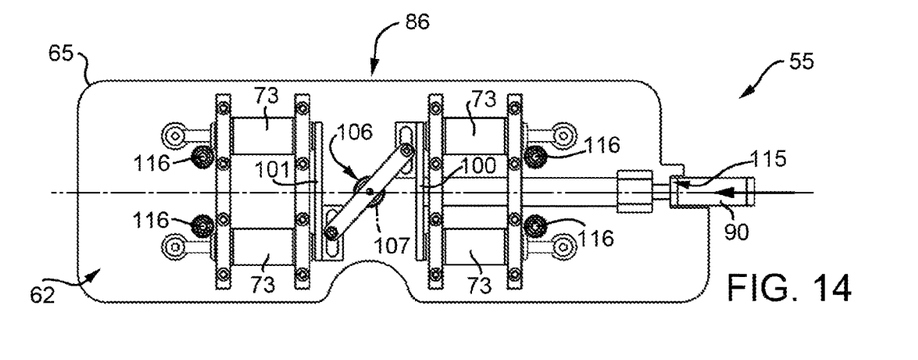

Release of the handle 90 causes the shaft 89 to return inside the cylinder 88, blocking the handle 90 inside the groove 115 (FIG. 14). In this way the blocking elements 73 are blocked in the blocking position.

In the non-limiting example described and illustrated here, the binding element 52 is preferably provided with a plurality of release elements 116 coupled to the plate 65 and configured to facilitate detachment between the recesses 15 and the protrusions 66. More specifically, the release elements 116 comprise pins partially housed in cylinders coupled to the supporting face 63 of the plate 65 and surrounded by springs.

Advantageously, the use of a cable moving device makes the system according to the present invention simple and reliable. The cable moving device is substantially selfcleaning and is therefore capable of ensuring correct movement of the carriage even in the presence of dust and processing residues.

Moreover, the use of a cable moving device makes the monitoring system according to the present invention very compact, particularly along the direction transversal to the circulating direction of the band 2. This aspect is very important as the spaces available, especially in the press section, are very limited.

Moreover, the use of protective covers drawn by the carriage ensures that the seat 31 of the guide 18 inside which the carriage 19 slides is kept clean and, in conditions of extreme use, also allows pressurisation of the seat 31.

Advantageously, the blocking device 55 is configured to block the detecting device 6 to the carriage 19 with the operation of a single actuator. Moreover, the carriage 19 and the detecting device are shaped so as to initially establish a geometric coupling between each other so as to facilitate subsequent blocking via the blocking device 55.

Finally, it is evident that modifications and variants can be made to the system and to the paper making machine described herein without however departing from the scope of the appended claims.

The invention claimed is:

1. A monitoring system for monitoring the condition of a band (2) circulating in a paper making machine (3); the system (1) comprising:
   a detecting device (6) configured to detect at least one parameter indicative of the conditions of the band (2); and
   a moving assembly (7) configured to move the detecting device (6) along a direction (A) transversal to the circulating direction (S2) of the band (2) and comprising a cable moving device (20);
   wherein the moving assembly (7) comprises a carriage (19) moved by the cable moving device (20) and coupled to the detecting device (6); and
   wherein the detecting device (6) is provided with a first binding element (11) and the carriage (19) is provided with a second binding element (52); the system comprising a blocking device (55) configured to selectively fix the first binding element (11) to the second binding element (52).

2. System according to claim 1, wherein the moving assembly (7) comprises a guide (18) configured to guide the movement of the carriage (19) and extending along an axis (A) substantially transversal to the circulating direction (S2) of the band (2).

3. System according to claim 1, wherein the cable moving device (20) comprises a hauling cable (43), a moving member (40), a moving pulley (41) moved by the moving member (40), and at least one return pulley (42).

4. System according to claim 3, wherein the carriage (19) comprises at least one grip member (54) configured to hook the carriage (19) to the hauling cable (43).

5. System according to claim 2, wherein the guide (19) comprises a guide element (26) suited to define a seat (31) in which the carriage (19) moves.

6. System according to claim 5, wherein the guide element (26) has a substantially C-shaped section.

7. System according to claim 5, wherein the guide (19) comprises a stiffening element (35) coupled to the guide element (26).

8. System according to claim 1, wherein the blocking device (55) comprises a plurality of blocking elements (73) and an actuator (74) configured to operate simultaneously the blocking elements (73) between an unblocking position wherein the first binding element (11) is not fixed to the second binding element (52) and a blocking position wherein the first binding element (11) is fixed to the second binding element (52).

9. System according to claim 8, wherein the first binding element (11) and the second binding element (52) are shaped so as to define a geometric coupling between each other.

10. Paper making machine comprising at least one band (2) circulating along a circulating direction (S2) and at least one monitoring system (1) for monitoring the conditions of the band (2) as claimed in claim 1.

\* \* \* \* \*